United States Patent [19]

Vincent et al.

[11] 4,059,621

[45] Nov. 22, 1977

[54] SUBSTITUTED BENZAMIDO PROPANOLAMINES

[75] Inventors: Michel Vincent, Bagneux; Georges Rémond, Versailles; Michel Laubie, Vaucresson, all of France

[73] Assignee: Science Union et Cie, Societe Francaise de Recherche Medicale, Suresnes, France

[21] Appl. No.: 379,529

[22] Filed: July 16, 1973

[30] Foreign Application Priority Data

July 21, 1972 United Kingdom ............... 34213/72

[51] Int. Cl.[2] .................. C07C 103/22; C07C 103/26; C07C 103/28; C07C 103/29; C07C 103/76; A61K 31/165

[52] U.S. Cl. ................................ 260/558 R; 544/106; 260/268 R; 424/248.54; 260/268 H; 260/268 CN; 260/306.7 R; 260/307 F; 260/326.12 R; 260/326.13 R; 260/327 R; 260/340.3; 260/340.5 R; 260/465 D; 260/501.17; 260/501.19; 260/556 C; 260/558 A; 260/558 D; 260/558 P; 260/559 R; 260/559 S; 260/559 A; 260/559 P; 424/246; 424/262; 424/267; 424/270; 424/272; 424/275; 424/278; 424/304; 424/316; 424/321; 424/324

[58] Field of Search ............. 260/558 R, 558 P, 570.7, 260/559 R, 559 P, 558 A, 558 D, 559 S, 559 A

[56] References Cited

U.S. PATENT DOCUMENTS

| | | | |
|---|---|---|---|
| 2,681,932 | 6/1954 | Dornfeld et al. | 260/570.7 X |
| 2,895,995 | 7/1959 | Willey et al. | 260/570.7 X |
| 3,205,136 | 9/1965 | Tedeschi | 260/570.7 X |
| 3,726,870 | 4/1973 | Rey-Bellet et al. | 260/558 R X |
| 3,808,213 | 4/1974 | Clemence et al. | 260/558 R X |
| 3,906,040 | 9/1975 | Vincent et al. | 260/558 R |
| 3,925,446 | 12/1975 | Köppe et al. | 260/558 P X |

OTHER PUBLICATIONS

"β-Adrenergic Blocking Agents", Crowther et al., Part II, *J. Med. Chem.* (11), 1968, pp. 1009–1013.

*Medicinal Chemistry*, Burger, 3rd Ed., Part II, Wiley Interscience (1970), pp. 1051, 1084.

Crowther et al. II, J. Med. Chem. (12), 1969, pp. 638–642.

*Primary Examiner*—Daniel E. Wyman
*Assistant Examiner*—Thomas A. Waltz
*Attorney, Agent, or Firm*—Behr & Woodbridge

[57] ABSTRACT

This invention relates to propanol derivatives and to a process for their preparation.

6 Claims, No Drawings

SUBSTITUTED BENZAMIDO PROPANOLAMINES

The present invention provides a compound of the general formula I, or an acid addition salt thereof:

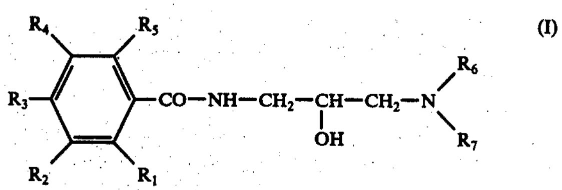

wherein:

$R_1$ represents a hydrogen or halogen atom, an alkyl, alkenyl, alkoxy or an alkenyloxy radical having from 1 to 5 carbon atoms, a cyano radical or carbamoyl radical;

$R_2$ represents a hydrogen atom, a hydroxy radical, an alkoxy radical having from 1 to 5 carbon atoms or an arylalkoxy radical wherein the alkoxy moiety has from 1 to 5 carbon atoms;

$R_3$ represents a hydrogen atom, a hydroxy radical, an alkoxy radical having from 1 to 5 carbon atoms, an arylalkoxy radical wherein the alkoxy moiety has from 1 to 5 carbon atoms, a nitro radical or an amino radical; or $R_1$ and $R_2$ together or $R_2$ and $R_3$ together represent a carbocyclic moiety which may include one or two heteroatoms and having from 5 to 7 bonds;

$R_4$ represents a hydrogen or halogen atom, a hydroxy radical, an alkoxy radical having from 1 to 5 carbon atoms, an arylalkoxy radical wherein the alkoxy moiety has from 1 to 5 carbon atoms, a sulphamoyl radical or an N, N-dialkylsulphamoyl radical;

$R_5$ is selected from the group consisting of hydrogen, halogen and alkyl radicals having from 1 to 5 atoms;

$R_6$ is selected from the group consisting of a hydrogen atom, a lower alkyl radical, a lower alkenyl and benzyl;

$R_7$ is selected from the group consisting of a lower alkyl radical, a lower alkenyl, a lower alkynyl or an aryl lower alkyl radical; or $R_6$ and $R_7$ together with the nitrogen atom to which they are bonded form a heterocyclic structure having from 5 to 7 bonds and may include another heteroatom.

The present invention also provides the acid addition salt thereof with a mineral or organic acid.

As far as the invention is concerned, the term lower alkyl is intended to designate a hydrocarbyl residue having from 1 to 6 carbon atoms in straight or branched chain which may be substituted by a hydroxyl, a lower alcoxy or a di-lower alkyl amino group. Examples of such lower alkyl are methyl, ethyl, iso propyl, sec butyl, neo pentyl, ter butyl or n-hexyl.

The term halogen designates preferably fluorine or chlorine. It may be also bromine or iodine.

The term lower alkenyl designates a hydrocarbyl residue with one or several double bonds having from 2 to 10 carbon atoms in straight or branched chain. Examples of such alkenyl are allyl, methallyl, isopentenyl, dimethyl allyl, butenyl, triallyl methyl, and the like.

The term lower alkoxy designates preferably an alkyloxy radical wherein the alkyl residue has from 1 to 6 carbon atoms.

The term aryl lower alkyl designates a phenyl -or a substituted phenyl-bearing a hydrocarbyl residue having from 1 to 4 carbon atoms. The hydrocarbyl residue may be straight or branched chain. The phenyl ring may carry substituent or substituents such as methoxy, trifluoromethyl, chloro. Examples of such aryl (lower alkyl) radicals are 3,4-dimethoxy benzyl, benzyl, m-trifluoromethyl benzyl, α-methyl benzyl, p-chlorobenzyl, phenylethyl, phenyl propyl or βmethyl phenylethyl.

The term lower alkynyl designates a hydrocarbon residue having a triple bond, having from 2 to 6 carbon atoms such as ethynyl, propyn-1 yl propyn-2 yl or methyl-1 butyn-2 yl.

The nitrogenous heterocycle may be pyrrolidine, piperidine or hexamethylene imine. It may also include an other heteroatom such as a nitrogen atom, a sulfur atom or an oxygen atom. Examples of such heterocycles are oxazolidine, morpholine, thiazolidine, thiamorpholine, piperazine, or homo morpholine. These heterocycles may carry also one or several alkyl residues.

When $R_1$ and $R_2$ or $R_2$ and $R_3$ together represent a carbocyclic moiety, they may form a structure such as —CHCH—CHCH, —CHCH—NH—, —S—$CH_2$—$CH_2$, O—$CH_2$—O—, or —O—$CH_2$—$CH_2$—O—. In these cases, the compounds of general formula I are derivatives of β-naphthalene, β-naphthalene, indole, thiochroman, or benzodioxole.

The present invention also provides a process for the preparation of a compound of the general formula I, which comprises reacting a compound of the general formula II

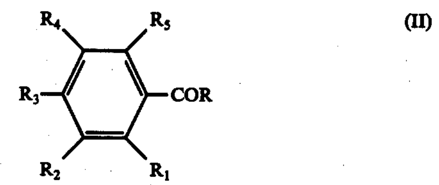

wherein $R_1$, $R_2$, $R_3$, $R_4$ and $R_5$, have the meanings given above, and R represents a halogen atom, for example a chlorine or bromine atom, a hydroxyl radical, an alkoxy radical having from 1 to 5 carbon atoms or an —O—CO—R' radical wherein R' represents a halogen atom or an alkyl radical having from 1 to 5 carbon atoms with a compound of the general formula III:

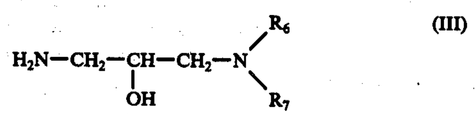

wherein $R_6$ and $R_7$ have the meaning given above or $R_6$ and $R_7$ together with the nitrogen atom to which they are bonded represent a heterocyclic structure having from 5 to 7 bonds and may include another heteroatom, in order to give a compound of general formula IV:

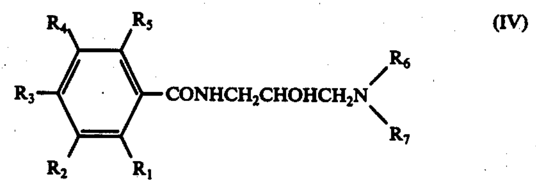

which, when $R_6$ is a benzyl radical, may be debenzylated by means of hydrogenolysis or acidolysis to provide a compound of general formula V:

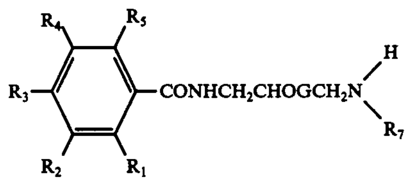

(V)

wherein the substituents $r_1$, $R_2$, $R_3$, $R_4$, $R_5$ and $R_7$ are defined as above.

When desired, the compounds of general formula I are salified by adding a mineral or organic acid.

The compounds of general formula I contain at least one asymetric carbon atom and may be resolved into optical isomers by combination with an optically-active acid.

The compounds of the present invention are bases which may be converted with acids into acid addition salts. As acids which may be used to form these salts, there may be especially mentioned, for example, in the mineral series, hydrochloric, hydrobromic, sulphuric and phosphoric acids, and in the organic series, acetic, propionic, maleic, fumaric, tartaric, citric, oxalic, benzoic, methanesulphonic and isethionic acids.

The compounds of the general formula I and physiologically tolerable salts thereof posses valuable pharmacological and therapeutic properties, especially cardiovascular, more particularly antiarrhythmic, cardiodepressive, vaso-dilating and antihypertensive properties and furthermore, anticholinergic and local anaesthetic properties, which render them suitable for use as medicines.

The present invention also provides a pharmaceutical preparation containing a compound of the general formula I or a physiologically tolerable salt thereof in admixture or conjunction with a pharmaceutically suitable carrier. The pharmaceutical preparation is preferably in unit dosage form.

The invention also relates to pharmaceutical compositions comprising as active ingredient one or more compounds of general formula I together with an inert non-toxic pharmaceutical carrier.

The pharmaceutical compositions are those suitable for administration by oral, parenteral, sublingual or rectal way, for example ampuls, phials, multidodoses flasks, tablets, coated tablets, granules, gelules, capsules, sublingual tablets, drinkable solutions or emulsions and suppositories.

They are prepared by known methods.

The dosages may vary broadly depending of the age of the patient, the therapeutic uses and the way of administration. By the adult, the unit dosage may vary from 25 mg to 150 mg. The normal daily dosage ranges from 50 to 750 mg depending of the nature of the disease and the age of the patient.

The 1,3-diamino propanols-2 of general formula II are all the most new compounds.

They may be conveniently obtained by hydrolysing a substituted phthalimide of the formula VI:

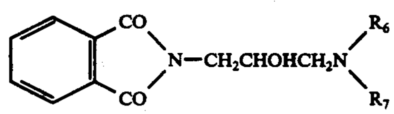

(VI)

wherein $R_6$ and $R_7$ are defined as above, by means of a mineral acid according to the procedure described by D.J. Triggle and B. Belleau Canad. J. of Chem. 40 (1962) 1215;

by means of haydrazine according to the procedure described by B.R. Baker J. of Am. Chem. Soc. 77 (1955) 5908 ;

by means of phenylhydrazine according to the procedure described by Boissonas Nature 169 (1952) 154;

by means of methyl hydrazine or 2,5-dichlorophenylhydrazine according to the procedure described by A.F. Rosenthal J. Org. Chem. 22 (1957) 89, to obtain a 1,3-diamino propanol-2 of general formula III in which $R_6$ and $R_7$ are defined as above, or by opening the oxirane ring of a 1,2-epoxy 3-amino propane of formula VII

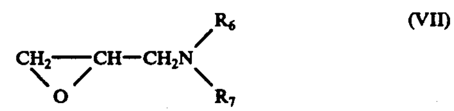

(VII)

wherein $R_6$ and $R_7$ are defined as above, with ammonia, to obtain a compound of general formula III using a procedure similar to that described by E.A. Steck J. of Am. Chem. Soc. 70 (1948) 4063.

The starting 1,2-epoxy 3-diamino propanes of general formula VII are obtained in a process similar to that described by Steck by condensing the appropriate amine of formula VII:

$$HN(R_6)(R_7) \quad (VIII)$$

$R_6$ and $R_7$ being defined as above, with epichlorhydrin.

The starting substituted phtalimides are prepared by condensing N-(2,3-epoxy propyl) phtalimide with an amine having the formula:

$$HN(R_6)(R_7) \quad (VIII)$$

(wherein $R_6$ and $R_7$ are defined as above) in an inert solvent and recovering said substituted phtalimide.

The present invention relates further to a method of treatment which consists in administering to warm-blooded animals suffering of cardio-vascular diseases a safe but efficient dosis of a compound of general formula I.

More particularly the present invention relates to a method for treating cardiac arythmias which consists in administering to warm-blooded animals suffering of said ilness a safe but effective amount of a compound of general formula I alone or in admixture with a medicine having similar or synergistic properties.

In most of the cases the effective dosage lies between 25 and 150 mg which may be renewed once to five times a day.

The present invention also provides a treatment pack comprising a compound of the invention, especially in the form of a pharmaceutical preparation, together with instructions, the instructions requiring that the compound be administered in effective doses to the warm-blooded animal to be treated. The following examples illustrate the invention. The melting points were determined on a kofler block, unless otherwise stated.

EXAMPLE 1

1-(1-naphthyl carboxamido)-3-(N-benzyl isopropylamino)-2-propanol hydrochloride

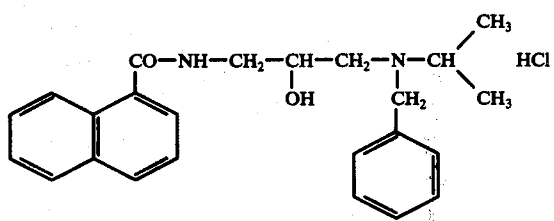

9.55 g (0.043 mole) of 1-amino-3-(N-benzyl isopropylamino)-2-propanol, prepared according to the method of Steck E.A. et al., (c.f. J. Am. Chem. Soc. 70, 4063-65 (1948) ) were added, while stirring and maintaining the temperature at +10° C, to a solution of 8.2 g (0.043 mole) of 1-naphthyl carbonyl chloride in 45 ml of anhydrous ether. The mixture was stirred at room temperature for 12 hours; the product was suction-filtered off, washed twice with 50 ml of anhydrous ether and then dried at room temperature under reduced pressure. There were obtained 17.4 g (0.042 mole) of 1-(1-naphthyl carboxamido)-3-(N-benzyl isopropylamino)-2-propanol as hydrochloride; M. Pt. 106° C (with decomposition).

EXAMPLES 2 to 12

The following derivatives were prepared by methods analogous to that described in example 1.

2. 1-(2-allyloxy benzamido)-3-(N-benzyl isopropylamino)-2-propanol hydrochloride, starting from 12.4 g (0.063 mole) of 2-allyloxy benzoyl chloride and 14.2 g (0.063 mole) of 1-amino-3-(N-benzyl isopropylamino)-2-propanyl (yield : 71%).

3. 1-(2-naphthyl carboxamido)-3-(N-benzyl isopropylamino)-2-propanol, M. Pt. 95° to 96° C, starting from 7.05 g (0.037 mole) of 2-naphthyl carbonyl chloride and 8.2 g (0.037 mole) of 1-amino-3(N-benzyl isopropylamino)-2 propanol. The crude hydrochloride is treated with an excess of aqueous potassium hydroxide in order to give the free base (overall yield 72 %).

4. 1-(2-naphthyl carboxamido)-3-(N-benzyl terbutylamino)-2 propanol hydrochloride, M. Pt. 185° C, starting from 19 g (0.1 mole) of 2-naphthyl carbonyl chloride and 23.6 g (0.1 mole) of 1-amino 3-(N-benzyl tert-butylamino)-2-propanol (yield : 88%).

5. 1-(4-nitro benzamido)-3-(N-benzyl isopropylamino)-2-propanol hydrochloride, M. Pt. 163°-164° C, starting from 7.2 g (0.039 mole) of 4-nitro benzoyl chloride and 8.65 g (0.039 mole) of 1-amino-3-(N-benzyl isopropylamino)-2-propanol (yield 71%).

6. 1-(1-naphthyl carboxamido)-3-(N-benzyl tert-butylamino)-2-propanol, M. Pt. 140° C, starting from 8.2 g (0.043 mole) of 1-naphthyl carbonyl chloride and 10.2 g (0.043 mole) of 1-amino-3-(N-benzyl tert-butylamino)-2-propanol. The crude hydrochloride is treated with an excess of aqueous potassium hydroxide in order to give the free base (yield : 89%).

7. 1-(8-thiochroman carboxamido)-3-(N-benzyl isopropylamino)-2-propanol, hydrochloride, M. Pt. 175° C, starting from 7.8 g (0.037 mole) of 8-thiochroman carbonyl chloride and 8.2 g (0.037 mole) of 1-amino-3-(N-benzyl isopropylamino)-2 propanol, (yield : 75%).

8. 1-(2-methoxy-5-sulphamoyl benzamido)-3-(N-benzyl isopropylamino)-2 propanol, M. Pt. 170° C (methanol) starting from 11.9 g (0.048 mole) of 2-methoxy-5-sulphamoyl benzoyl chloride and 10.7 g (0.048 mole) of 1-amino-3-(N-benzyl isopropylamino)-2-propanol. The crude hydrochloride was treated with an excess of aqueous potassium hydroxide in order to give the free base which was crystallized from methanol (yield : 82%).

9. 1-(2,6-dimethyl benzamido)-3-(N-benzyl tert-butylamino)-2-propanol hydrochloride, starting from 3.4 g (0.02 mole) of 2,6-dimethyl benzoyl chloride and 2.4 (0.02 mole) of 1-amino-3-(N-benzyl tert-butylamino)-2-propanol (yield : 91 %).

10. 1-(2,6-dichloro benzamido)-3-(N-benzyl tert-butylamino)-2-propanol, hydrochloride, starting from 10.4 g (0.05 mole) of 2,6-dichloro benzoyl chloride and 11.8 g (0.05 mole) of 1-amino-3-(N-benzyl tert-butylamino)-2-propanol (yield : 87 %).

11. 1-(3,4,5-trimethoxy benzamido)-3-(N-benzyl tert-butylamino)-2-propanol hydrochloride, starting from 7.8 g (0.034 mole) of 3,4,5-trimethoxy benzoyl chloride and 8 g (0.034 mole) of 1-amino-3-(N-benzyl tert-butylamino)-2-propanol (yield 78 %).

12. 1-(3,4-methylenedioxy benzamido)-3-(N-benzyl tert-butylamino)-2- propanol hydrochloride, starting from 6.3 g (0.034 mole) of 3,4-methylenedioxy benzoyl chloride and 8 g (0.034 mole) of 1-amino-3-(N-benzyl tert-butylamino)-2- propanol (yield 80 %).

EXAMPLE 13.

1-(naphthyl carboxamido)-3-isopropylamino-2-propanol

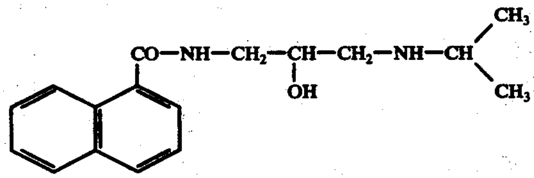

3 g of palladium on charcoal (10%) were added to a solution of 9.3 g (0.022 mole) of 1-(1-naphthyl carboxamido)-3-(N-benzyl isopropylamino-2-propanol hydrochloride, obtained as described in example 1, ml in 150 ml of ethanol.

The mixture was hydrogenated at room temperature, under a pressure of 4 kg/cm2, for 6 hours. The catalyst was filtered off, and the filtrate was evaporated under reduced pressure. The residue was taken up in 50 ml of water and the solution was acidified to a pH of 2 by adding N hydrochloric acid solution. Small amounts of insoluble matters are extracted with ether, and the aqueous phase was rendered alkaline with potassium carbonate. The crystalline base was suction-filtered off, was recrystallized from 50 ml of anhydrous ether, and was dried at room temperature under reduced pressure.

There were obtained 6 g of 1-(1-naphthyl carboxamido)-3-isopropylamino 2-propanol. The corresponding hydrochloride, M. Pt. 167° to 169° C with decomposition was prepared by treating the free base with a stoichioetric amount of a 0.1 N solution of hydrogen chloride in ether (yield 94 %).

EXAMPLES 14 to 22

The following derivatives were prepared by a similar method to that described in example 13.

14. 1-(2-allyloxy benzamido)-3-isopropylamino-2-propanol, M. Pt. 108°-109° C, starting from 23.5 g (0.056 mole) of 1-(2-allyloxy benzamido)-3-(N-benzyl isopropylamino)-2-propanol hydrochloride prepared as described in example 2 (yield 78 %).

15. 1-(2-naphthyl carboxamido)-3-isopropylamino-2-propanol hydrochloride, M.Pt. 158°-159° C (acetonitrile), starting from 11.2 g (0.03 mole) of 1-(2-naphthyl carboxamido)-3-(N-benzyl isopropylamino)-2-propanol hydrochloride prepared from the base described in example 3 (yield 80.5 %).

16. 1-(2-naphthyl carboxamido)-3-tert-butylamino-2-propanol hydrochloride, M. Pt. 200°-201° C (ethyl acetate), starting from 13.6 g (0.032 mole) of 1-(2-naphthyl carboxamido)-3-(N-benzyl tert-butylamino)-2-propanol hydrochloride prepared as described in example 4 (yield : 85.5 %).

17. 1-(4-amino benzamido)-3-isopropylamino-2-propanol hydrochloride, M. Pt. 135°-136° C (with decomposition) (ethyl acetate), starting from 5.5 g (0.0135 mole) of 1-(4-nitrobenzamido)-3-(N-benzyl isopropylamino)-2-propanol hydrochloride prepared as described in example 5 (yield 68 %).

18. 1-(1-naphthyl carboxamido)-3-tert-butylamino-2-propanol hydrochloride, M. Pt. 252°-253° C with decomposition (methanol), starting from 13.6 g (0.035 mole) of 1-(1-naphthyl carboxamido)-3-(N-benzyl tert-butylamino)-2-propanol hydrochloride prepared as described in example 6 (yield 90%).

19 1-(2,6-dimethyl benzamido)-3-tert-butylamino-2-propanol, M. Pt. 95°-96° C, starting from 8.1 g (0.02 mole) of 1-(2,6-dimethyl benzamido)-3-(N-benzyl tert-butylamino)-2-propanol hydrochloride prepared as described in example 9 (yield 70%). The corresponding hydrochloride, M. Pt. 205°-206° C (with decomposition) was prepared by treating the free base with a stoichiometric amount of a 0.1 N solution of hydrogen chloride in ether.

20. 1-(2,6-dichlorobenzamido)-3-tert-butylamino-2-propanol, M. Pt. 152°-153° C (benzene), starting from 22.2 g (0.05 mole) of crude 1-(2,6-dichloro benzamido)-3-(N-benzyl tert-butylamino)-2-propanol hydrochloride prepared as described in example 10 (yield 80 %). The corresponding hydrochloride was prepared as described in example 19, M. Pt. 220°-221° C (with decomposition).

21. 1-(3,4,5-trimethoxy benzamido)-3-tert-butylamino-2-propanol, M. Pt. 108°-109° C, starting from 15.8 g (0.034 mole) of 1-(3,4,5-trimethoxy benzamido)-3- (N-benzyl tert-butylamino)-2-propanol hydrochloride prepared as described in example 11 (yield 67.8 %).

22. 1-(3,4-methylenedioxy benzamido)-3-tert-butylamino-2-propanol, M. Pt. 84° to 85° C, starting from 14.3 g (0.034 mole) of 1-(3,4-methylenedioxy benzamido) -3-(N-benzyl tert-butylamino)-2-propanol hydrochloride prepared as described in example 12 (yield 41 %).

We claim:

1. A compound selected from the group consisting of:
- A propanol derivative having the formula I:

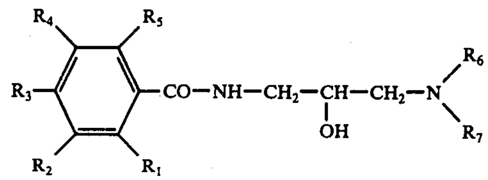

wherein:

$R_1$ represents a hydrogen or halogen atom, an alkyl, alkenyl, alkoxy or an alkenyloxy radical having from 1 to 5 carbon atoms, or carbamoyl radical;

$R_2$ represents a hydrogen atom, a hydroxy radical, an alkoxy radical having from 1 to 5 carbon atoms or a phenyl alkoxy radical wherein the alkoxy moiety has from 1 to 5 carbon atoms;

$R_3$ represents a hydrogen atom, a hydroxy radical, an alkoxy radical having from 1 to 5 carbon atoms, a phenyl alkoxy radical wherein the alkoxy moiety has from 1 to 5 carbon atoms, a nitro radical or an amino radical;

or $R_1$ and $R_2$ together or $R_2$ and $R_3$ together represent the —CH═CH—CH═CH moiety;

$R_4$ represents a hydrogen atom, $R_5$ is selected from the group consisting of alkyl radicals having from 1 to 5 carbon atoms;

$R_6$ is selected from the group consisting of a hydrogen atom, a lower alkyl radical, a lower alkenyl radical and a benzyl radical;

$R_7$ is selected from the group consisting of a lower alkyl radical, a lower alkenyl and a phenyl lower alkyl radical wherein the lower alkyl moiety has 1 - 5 carbon atoms.

2. A compound selected from the group consisting of: A propanol derivative having the formula:

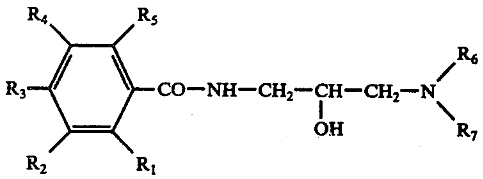

wherein:

$R_1$ represents a hydrogen or halogen atom, an alkyl, alkenyl, radical having from 1 to 5 atoms, or carbamoyl radical;

$R_2$ and $R_3$ represents a hydrogen atom, or $R_1$ and $R_2$ together or $R_2$ and $R_3$ together represent the —CH═CH—CH═CH moiety;

or $R_4$ represents a hydrogen atom, $R_5$ is selected from the group consisting of alkyl radicals having from 1 to 5 carbon atoms;

$R_6$ is selected from the group consisting of a hydrogen atom, a lower alkyl radical, a lower alkenyl radical and a benzyl radical;

$R_7$ is selected from the group consisting of a lower alkyl radical, a lower alkenyl, and a phenyl lower alkyl radical wherein the lower alkyl moiety has 1 - 4 carbon atoms.

3. A compound of claim 2 wherein $R_1$ and $R_2$ together represent the —CH═CH—CH═CH— moiety 4. A compound of claim 2 wherein $R_2$ and $R_3$ together represent the —CH═CH—CH═CH moiety.

5. A compound of claim 2, the 1-(2,6-dimethyl benzamido) 3-terbutylamino 2-propanol.

6. A compound of claim 2 having the formula 1-($2R_5$,$3R_4$ -naphthyl carboxamido)-3-($R_6$,$R_7$ -amino)-2-propanol, wherein $R_4$, $R_5$, $R_6$ and $R_7$ are as in claim 1.

* * * * *